US006726648B2

(12) United States Patent
Kaplon et al.

(10) Patent No.: US 6,726,648 B2
(45) Date of Patent: Apr. 27, 2004

(54) VALVED APICAL CONDUIT WITH TROCAR FOR BEATING-HEART VENTRICULAR ASSIST DEVICE PLACEMENT

(75) Inventors: Richard J. Kaplon, Miami Beach, FL (US); Gary S. Margules, Miami Beach, FL (US)

(73) Assignee: The University of Miami, Miami, FL (US)

( * ) Notice: Subject to any disclaimer, the term of this patent is extended or adjusted under 35 U.S.C. 154(b) by 0 days.

(21) Appl. No.: 09/928,472

(22) Filed: Aug. 14, 2001

(65) Prior Publication Data

US 2002/0045846 A1 Apr. 18, 2002

Related U.S. Application Data

(60) Provisional application No. 60/224,892, filed on Aug. 14, 2000.

(51) Int. Cl.[7] ................................................. A61M 5/00
(52) U.S. Cl. .................................................. 604/9; 604/8
(58) Field of Search ........................................ 604/8–10

(56) References Cited

U.S. PATENT DOCUMENTS

| | | | | |
|---|---|---|---|---|
| 4,769,031 A | | 9/1988 | McGough | 623/1 |
| 5,830,222 A | | 11/1998 | Makower | 606/159 |
| 5,882,344 A | * | 3/1999 | Stouder, Jr. | 604/264 |
| 5,984,956 A | | 11/1999 | Tweden | 623/1 |
| 6,053,896 A | | 4/2000 | Wilson | 604/247 |
| 6,254,564 B1 | * | 7/2001 | Wilk et al. | 604/9 |
| 6,343,605 B1 | * | 2/2002 | Lafontaine | 128/898 |

* cited by examiner

Primary Examiner—Angela D. Sykes
Assistant Examiner—Leslie R. Deak
(74) Attorney, Agent, or Firm—Nixon & Vanderhye PC

(57) ABSTRACT

An inflow cuff with trocar for apical cannulation of the heart. The inflow cuff has an omni-directional or unidirectional valve that prevents blood from flowing out of the heart, thus facilitating apical cannulation in beating-heart situations. The inflow cuff is particularly suited for use in ventricular assist device (VAD) implantation procedures, in which the trocar would be used to punch a hole in the apex, followed by immediate insertion of the inflow cuff. If used in a VAD implantation procedure, the valve of the inflow cuff prevents blood loss until an inflow conduit from the VAD is inserted.

20 Claims, 7 Drawing Sheets

VALVED APICAL CONDUIT WITH TROCAR FOR BEATING-HEART VENTRICULAR ASSIST DEVICE PLACEMENT

This application claims the benefit of earlier provisional Application No. 60/224,892, filed Aug. 14, 2000.

BACKGROUND OF THE INVENTION

1. Field of the Invention

The present invention relates generally to conduits for apical cannulation of the heart, and more specifically, to inflow cuffs for cannulation of the heart for ventricular assist device placement.

2. Description of Related Art

In the past, a patient requiring a heart transplant was forced to wait and hope that a suitable heart became available before he or she became too sick to undergo a transplant procedure. More recently, devices known as ventricular assist devices (VADs) have been developed. These devices are implantable, programmable pumps that assist the ventricles of the heart, usually the left ventricle, in pumping blood. The VAD presents both the physician and the patient with an alternative to the wait-and-hope approach of the past by allowing patients to be temporarily supported while awaiting transplant. Patients in whom a VAD has been implanted are typically healthy enough to undergo a transplant when a suitable heart becomes available. Studies have also shown that a VAD may be used for longer periods of time, e.g., more than a year.

However, the procedure to implant a VAD is a cardiothoracic surgical procedure, and as such, presents its own risk of complications. In a typical VAD implantation procedure, a "side-biting" clamp is applied to the aorta and the outflow conduit from the VAD is sewn into the aorta. A vascular clamp is placed across the distal portion of the outflow conduit after the "side-biting" clamp is removed in order to de-air the outflow conduit. Once the VAD outflow conduit is attached to the aorta, the inflow conduit is inserted into the apex of the heart. To place the inflow conduit, a hole is cored in the apex of the heart, and pericardial sutures are placed around the hole. After pericardial sutures are placed around the hole cored in the apex, an inflow cuff is inserted into the hole.

The inflow cuff is a short, relatively rigid connector that serves as an interface between the inflow conduit of the VAD and the ventricle. The inflow cuff is usually made of a biocompatible elastomer or plastic, such as silicone, which has been reinforced with a woven mesh. The woven mesh may be comprised of, e.g., woven polyester strands, and serves to rigidify the inflow cuff. A sewing ring made of synthetic felt (e.g., felt composed of poly (tetrafluoroethylene) or polyester strands) is typically provided around the external diameter of the inflow cuff so that the inflow cuff can be secured in the apex hole using the previously positioned pericardial sutures.

After the inflow cuff has been sewn into the apex of the heart, the inflow conduit from the VAD is passed through the inflow cuff and into the ventricle. The inflow cuff and inflow conduit are sized so that the inflow cuff has an internal diameter only slightly larger than the external diameter of the inflow conduit. Once the inflow conduit is inserted into the inflow cuff, the two form a snug fit such that there is essentially no clearance between the inflow conduit and inflow cuff. A simple tie-down is secured around the outer diameter of the inflow cuff to hold the inflow conduit in place.

Following the successful insertion of the inflow conduit into the inflow cuff, blood is permitted to egress the VAD via the outflow conduit and the heart is de-aired. Once the heart has been de-aired, the VAD is turned on and begins to operate.

Although the typical VAD implantation procedure uses an inflow cuff, as described above, to cannulate the apex of the heart, various other devices are known for apical cannulation of the heart, establishing access to the coronary vessels, or controlling blood flow from the heart.

For example, U.S. Pat. No. 4,769,031 to McGough et al. discloses a ventricular access device which is comprised of a conduit and grommet that are inserted into the base of the heart and fed though to the apex such that the left ventricle is cannulated in an inside-to-outside manner. The conduit includes a sharpened, retractable, conical end to facilitate penetration of the left ventricle and a grommet to hold the conduit in place. The grommet disclosed by this patent is complex, and the device has found little clinical applicability.

U.S. Pat. No. 6,053,896 to Wilson et al. discloses an apparatus suitable for a left ventricular drain line. The apparatus includes a duck-bill check valve to avoid pressure overload. The check valve opens in an outward direction to prevent blood from flowing back towards the heart. The apparatus is designed for extracorporeal use only; it does not include structure suitable for cannulation of the left ventricle.

Other devices available include that disclosed by U.S. Pat. No. 5,984,956 to Tweden et al., which describes an alternate type of apparatus for establishing blood flow between a chamber of the heart and one of the coronary vessels. The apparatus is a rigid conduit tube with a beveled end to aid in the penetration of cardiac tissue. It includes neither valve nor trocar, and there is no mention that backflow of blood into the heart may be a problem.

A more generally applicable device is disclosed by U.S. Pat. No. 5,830,222 to Makower, which describes a device and method for transvascular access. The disclosed method and device allow the vascular system to be used as a conduit for other procedures. Additionally, a number of hemostasis-type valves are known for arterial catheterization. However, none of these devices appears to designed for implantation directly into the heart.

A major difficulty with the typical VAD implantation procedure, and most other procedures requiring apical cannulation, is that the heart must be stopped, which requires that the patient be placed on cardiopulmonary bypass (CPB). If the heart is beating while the procedure is performed, the patient will exsanguinate (i.e., a large volume of blood will escape through the inflow cuff before the inflow conduit can be placed). Unfortunately, CPB carries with it an inherent risk of mortality, a risk that is especially acute in a critically ill patient requiring a VAD. Therefore, a need exists for an improved means of implanting a VAD without requiring the use of CPB.

SUMMARY OF THE INVENTION

One aspect of the claimed invention relates to an inflow cuff for beating-heart apical cannulation of a heart. The inflow cuff comprises a tube having a first end and a second end. The first end of the tube is constructed and adapted to be inserted into the heart. A sewing ring is disposed on an exterior surface of the tube proximate to the first end. The sewing ring is constructed and adapted to be sutured to an exterior wall of the heart and to retain the first end of the tube at a selected position in the heart. The inflow cuff also comprises a valve disposed on and integral with the interior of the tube. The valve has two or more compliant leaves constructed and adapted to form a releasable seal with one another. The valve prevents blood flow out of the heart when closed and opens in response to pressure directed towards the heart. The valve is disposed further from the first end of the tube than the sewing ring. Additionally, the inflow cuff is constructed and arranged to allow the passage of a trocar through its lumen, wherein the trocar is constructed and arranged to form a hole in the heart of sufficient size to admit the first end of the inflow cuff. The inflow cuff is further constructed and arranged to permit the withdrawal of the trocar and the insertion of a conduit through the lumen of the inflow cuff to establish a route for blood flow out of the heart.

Another aspect of the claimed invention relates to a medical device which may be inserted into the heart of a patient to provide a passageway for bloodflow, specifically bloodflow in a conduit. The medical device comprises an inflow cuff with a valve. The valve prevents blood from flowing out of the heart when closed and opens in response to pressure in the lumen of the inflow cuff directed inward toward the heart. The claimed invention also includes a trocar which is inserted longitudinally through the lumen of the inflow cuff and extends beyond the end of the inflow cuff. The trocar is removable from the lumen of the inflow cuff. The lumen of the inflow cuff is sized to allow the insertion of a conduit into the heart.

A further aspect of the claimed invention relates to a method for providing a passageway for bloodflow out of the heart of a patient. The method comprises inserting an inflow cuff according to the claimed invention into the heart, retracting the blade of the trocar and removing it from the inflow cuff and inserting an inflow conduit through the lumen of the inflow cuff to open the valve. The valve may be a unidirectional or an omni-directional valve. The inflow conduit inserted may be the inflow conduit of a ventricular assist device (VAD).

BRIEF DESCRIPTION OF THE DRAWINGS

Various exemplary embodiments will be described with reference to the following drawings, in which like reference characters represent like features, wherein.

DETAILED DESCRIPTION OF THE PREFERRED EMBODIMENTS

Figure 1:
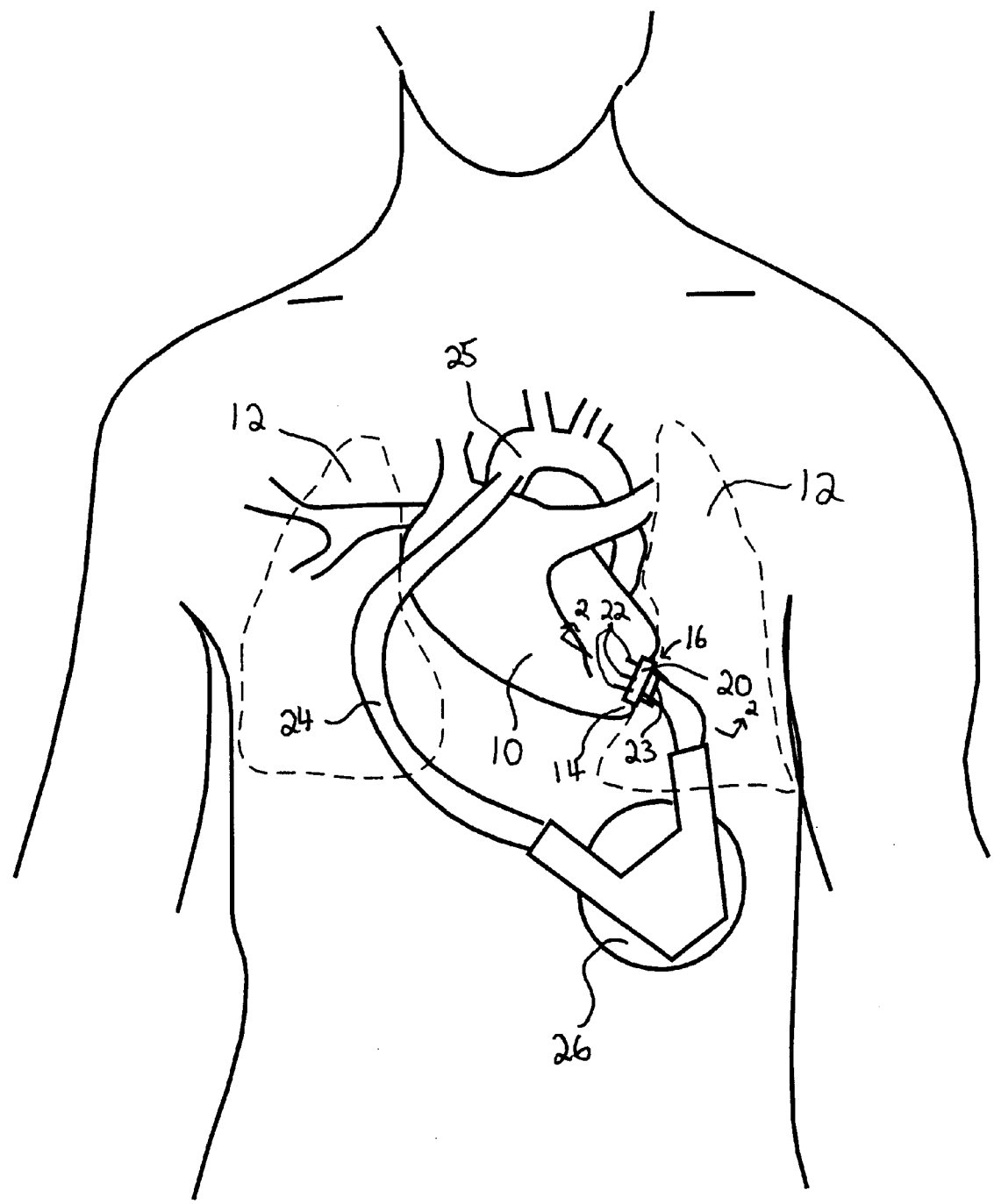
FIG. 1 is a perspective view of the an inflow cuff according to the present invention installed along with a ventricular assist device in a patient.

FIG. 1 is a perspective view of an inflow cuff 16 according to the present invention, installed along with a ventricular assist device (VAD) 26 in a patient. The view of FIG. 1 has been simplified for the purposes of illustration; the ribcage, sternum and pericardium are not shown in FIG. 1. The heart 10 is shown in the center of FIG. 1, bordered on the right and left by the lungs 12, which have been retracted away from the heart 10 in the view of FIG. 1. In the view of FIG. 1, the apex of the heart, indicated at 14, is cannulated, and inflow cuff 16 can be seen protruding from the apex 14. The inflow conduit 18, which is a part of the VAD 26, is inserted into the inflow cuff 16. A sewing ring 20 comprised of synthetic felt is attached to the exterior of the inflow conduit 18 and abuts the surface of the apex 14. Pericardial sutures 22 extend from the sewing ring 20 into the apex 14, securing the inflow cuff in place. A tie 23 is secured around inflow cuff 16 to hold the inflow conduit 18 in place.

As shown in FIG. 1, the outflow conduit 24 of the VAD 26 is sewn into the ascending aorta 25, while the VAD 26 itself may rest either in the chest or abdominal cavities of the patient, depending on the particular model of VAD 26 that is used with the inflow cuff 16. The VAD 26 may be electrically or pneumatically powered, and may also include a battery pack or other external appliances or connections, which are not shown in FIG. 1. It should be understood that the inflow cuff 16 according to the present invention may be used with any model of VAD, or alternatively, with any other medical device which requires apical cannulation of the heart in order to operate.

Figure 2:
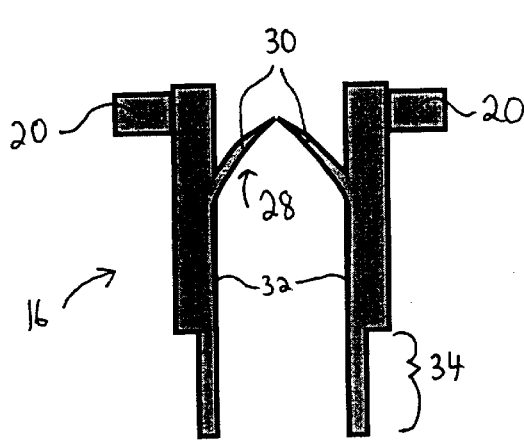
FIG. 2 is a sectional view of an inflow cuff according to a first embodiment of the invention, through line 2—2 of FIG. 1, without an inflow conduit or trocar inserted.

FIG. 2 is a sectional view of the inflow cuff 16 along Line 2—2 of FIG. 1. In FIG. 2, the inflow conduit 18 from the VAD 26 is not shown. As is shown in FIG. 2, the inflow cuff 16 has a unidirectional valve 28 located just behind the sewing ring 20 which prevents blood flow out of the heart until the inflow conduit 18 is inserted into the inflow cuff 16. According to a first embodiment of the invention, the unidirectional valve 28 of the inflow cuff 16 is of a "duck bill" type, and has two leaves 30 which extend from the inner wall 32 of the inflow cuff 16 and meet at the center of the inflow cuff 16, forming a releasable seal with one another.

Figure 3:
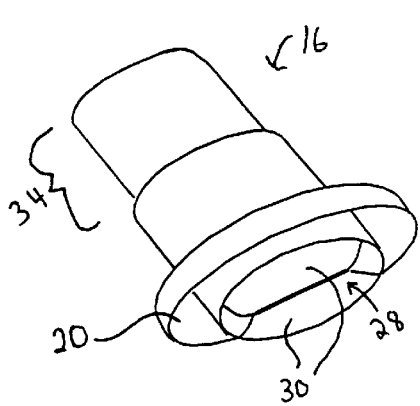
FIG. 3 is a perspective view of the inflow cuff of FIG. 2 from its insertion end.

FIG. 3 is a perspective view of the inflow cuff 16 from its insertion end, that is, the end extending into the apex 14 in FIG. 1. The two leaves 30 abut each other, forming the closed position of the unidirectional valve 28. Although only two leaves 30 are illustrated in FIGS. 2 and 3, it is contemplated that the unidirectional valve 28 may include three or more leaves 30. In FIGS. 2–3, the sewing ring 20 is visible on the exterior surface of the inflow cuff 16.

As is evident from FIGS. 1–3, the inflow cuff 16 narrows beyond the unidirectional valve 28. This narrowed portion 34 is of a diameter suitable for forming a snug fit with the inflow conduit 18 to retain the inflow conduit 18 within the inflow cuff 16 during the operation of the VAD 26.

According to the first embodiment of the invention, the inflow cuff 16 is constructed of a reinforced, medical grade of silicone rubber, such as SILASTIC® (Dow Corning Corporation, Midland, Mich.), which has a woven mesh embedded within. The woven mesh may be comprised of polyester threads, or another synthetic thread material, such as KEVLAR® (DuPont, Inc., Wilmington, Del.). The woven mesh rigidifies the inflow cuff 16 and gives it increased toughness and tear resistance, while allowing the material to retain some degree of compliance. The sewing ring 20 is comprised of a synthetic felt material that is made from a material such as woven poly(tetrafluoroethylene) or polyester strands.

According to a second embodiment of the invention, the inflow cuff 16 is constructed of a more rigid thermoset or thermoplastic polymer, such as a medical grade of polycarbonate. This second embodiment may be particularly useful when the inflow cuff 16 is to be used for a long period of time. In either of the first or second embodiments, the narrowed portion 34 may be formed of a different material than that of the rest of the inflow conduit 16, such as an unreinforced, medical grade silicone rubber.

Because the inflow cuff 16 includes a unidirectional valve 28 that prevents blood from flowing out of the heart 10 before the inflow conduit 18 is inserted into the inflow cuff 18, the inflow cuff 16 is particularly suited for a beating-heart VAD implantation procedure.

In a beating-heart type of VAD implantation procedure, the typical technique for creating a hole in the apex 14 (i.e., coring a hole with scissors and other instruments and then leaving the hole open while pericardial sutures and an inflow cuff are placed) is unsuitable, as this technique would cause the patient to exsanguinate before the procedure is complete. Therefore, the inflow cuff 16 is sized to allow the passage of a trocar 38 through its interior, past the unidirectional valve 28. The trocar 38 can be used to "punch" a hole in the apical tissue, allowing immediate insertion of the inflow cuff 16 into the heart. Once the inflow cuff 16 is inserted into the apex 14, the trocar 38 is retracted and withdrawn from the inflow cuff 16.

Figure 4:
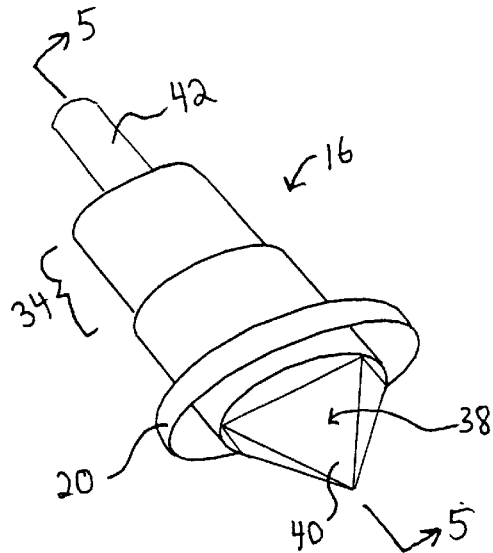
FIG. 4 is a perspective view of the inflow cuff of FIG. 3 with a trocar fully inserted.

FIG. 4 is a perspective view of the inflow cuff 16 showing a trocar 38 fully inserted therein. The trocar 38, as shown, has a sharpened, pyramidal portion 40 that allows the surgeon to punch a hole in the apex 14 and immediately insert the inflow cuff 16. The trocar 38 is subsequently withdrawn from the inflow cuff 16. Many types of trocars 38 are known in the art, and therefore, a surgeon may select a trocar 38 having a different sharpened portion than the sharpened, pyramidal portion 40 depicted in FIG. 4. In particular, a trocar having a three-sided sharpened, pyramidal portion is also particularly suitable.

Figure 5:
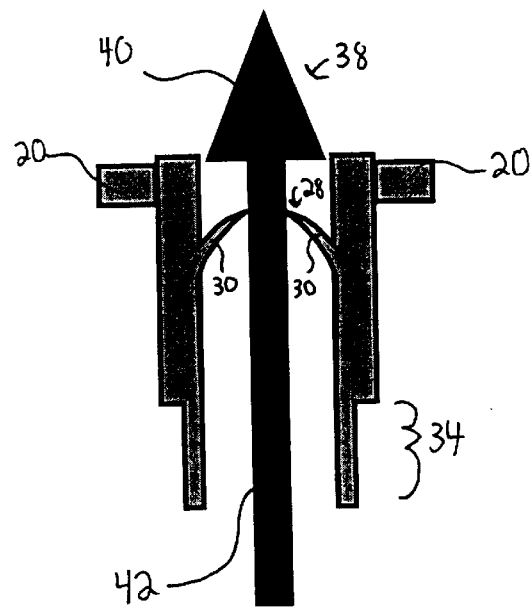
FIG. 5 is a sectional view of the inflow cuff of FIG. 4 with a trocar inserted, through line 5—5 of FIG. 4.

FIG. 5 is a sectional view through line 5—5 of FIG. 4, illustrating the inflow cuff 16 with a trocar 38 inserted. As shown, the handle portion 42 of the trocar 38 is rigidly connected to the sharpened, pyramidal portion 40 and extends from the protruding sharpened, pyramidal portion 40, through the unidirectional valve 28 and out the narrowed portion 34 of the inflow cuff 16. The leaves 30 of the unidirectional valve 28 deform around the handle portion 42, forming a seal with the trocar 38 inserted. The trocar 38 may be of any size and its handle portion 42 of any diameter, so long as the trocar 38 is able to pass through the inflow cuff 16, and particularly, through the unidirectional valve 28, without causing damage.

Figure 6:
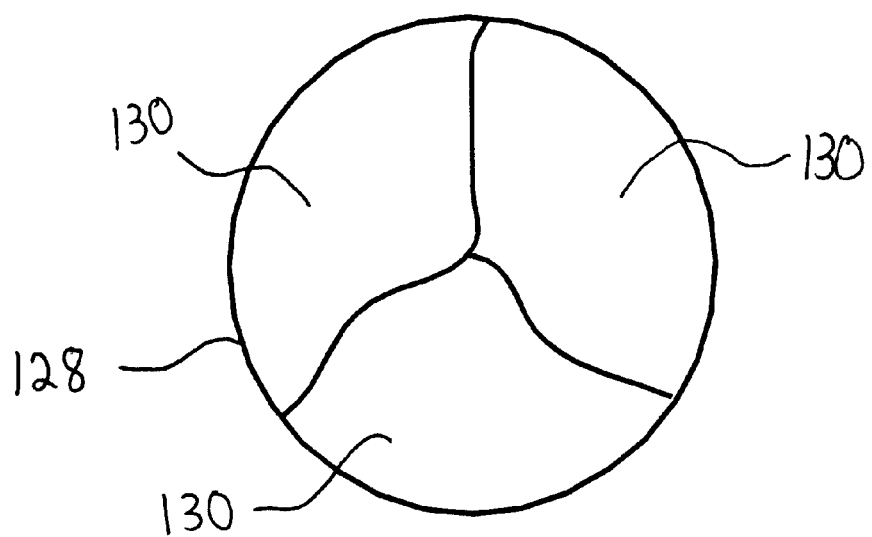
FIG. 6 is a plan view of a valve according to a third embodiment of the present invention.

According to a third embodiment of the invention, an inflow cuff 116 includes a valve 128 having three leaves 130 that meet to form a seal. As in the first and second embodiments, the leaves 130 may be made of unreinforced or reinforced SILASTIC® rubber, or alternately, another biocompatible silicone rubber. The leaves 130 of the third embodiment are thicker than the leaves 30 of the first and second embodiments, and may be less prone to inversion or damage when a trocar is inserted through them. FIG. 6 is a plan view of the valve 128, illustrating the placement of the three leaves 130.

Figure 7:
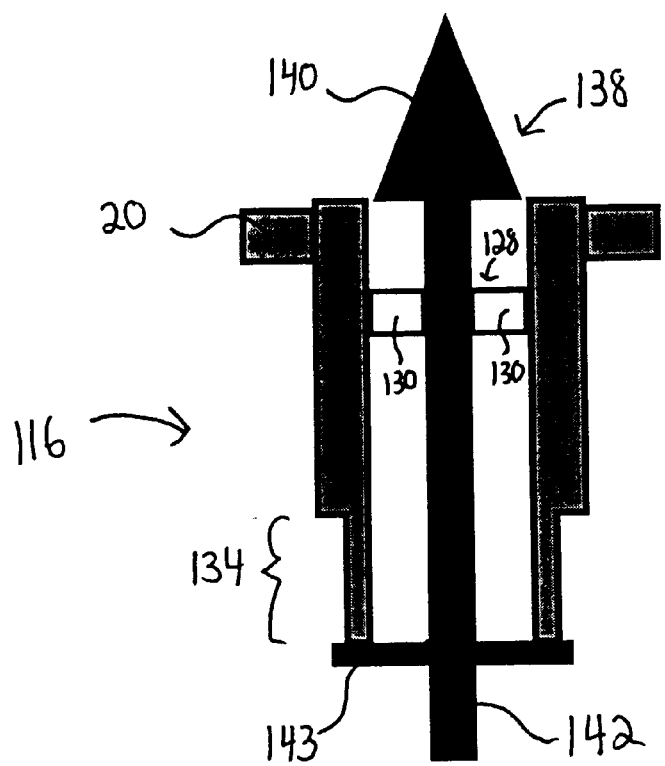
FIG. 7 is a sectional view through line 2—2 of FIG. 1 of an inflow cuff according to the third embodiment of the present invention.

FIG. 7 is a sectional view of the inflow cuff 116 with trocar 138 inserted, once again through line 2—2 of FIG. 1. As is clear from FIGS. 6 and 7, the valve 128 installed in inflow cuff 116 is essentially omni-directional. In other words, the placement of the leaves 130 and their thickness allows the valve 128 to be unbiased, i.e., to resist force applied in either direction.

FIG. 7 also illustrates an advantageous feature of the trocar 138. When using an inflow cuff 16 according to the first and second embodiments of the invention, the surgeon needs to control the insertion of the trocar 38 very carefully to ensure that the trocar 38 does not penetrate too far into the heart 10. If the trocar 38 did penetrate too far into the heart 10, it could potentially do internal damage, thus complicating the surgical procedure.

However, the trocar 138 includes a flange 143 near the end of the handle portion 142. The flange 143 is wider than the diameter of the narrowed portion 134 of the inflow cuff 116, such that the flange 143 forms a "stop", preventing the trocar 138 from being inserted into the inflow cuff 116 further than the position of the flange 143. The position at which the flange 143 is installed would be determined by the characteristics of the sharpened, pyramidal portion of the trocar 140 as well as the characteristics of the patient's heart 10. (For example, a patient with advanced cardiac hypertrophy may have a very thick ventricular wall, and may require deeper penetration of the trocar 138.) It is contemplated that the flange 143 may be an integrally formed portion of the handle portion 142, or alternately, it may be adjustably attached to the handle portion 142, e.g., by set screws or other fasteners.

To provide even better control over the trocar 138, the handle portion 142 is knurled, textured, or otherwise modified so that the surgeon can maintain a good grip on the trocar 138. It is also contemplated that the end of the handle portion 142 could be molded into a grip-shape, in which case the bottom of the grip-shape could define the flange 143.

The inflow cuff 16, 116 and trocar 38, 138 are best used in a method for cannulating the apex of the heart without cardiopulmonary bypass (CPB). One example of such a method 200 is given below and with reference to FIG. 7. Method 200 is equally applicable to inflow cuffs 16, 116 and trocars 38, 138 according to the first, second, and third embodiments of the invention, although, except as noted, only the features of the inflow cuff 16 and trocar 38 are described.

Example

Method for Apical Cannulation Without CPB

In this example, it is assumed that the patient requires only left ventricular support, although the inflow cuff 16 and trocar 38 according to the present invention may be used for either left or right ventricular cannulation.

Figure 8:
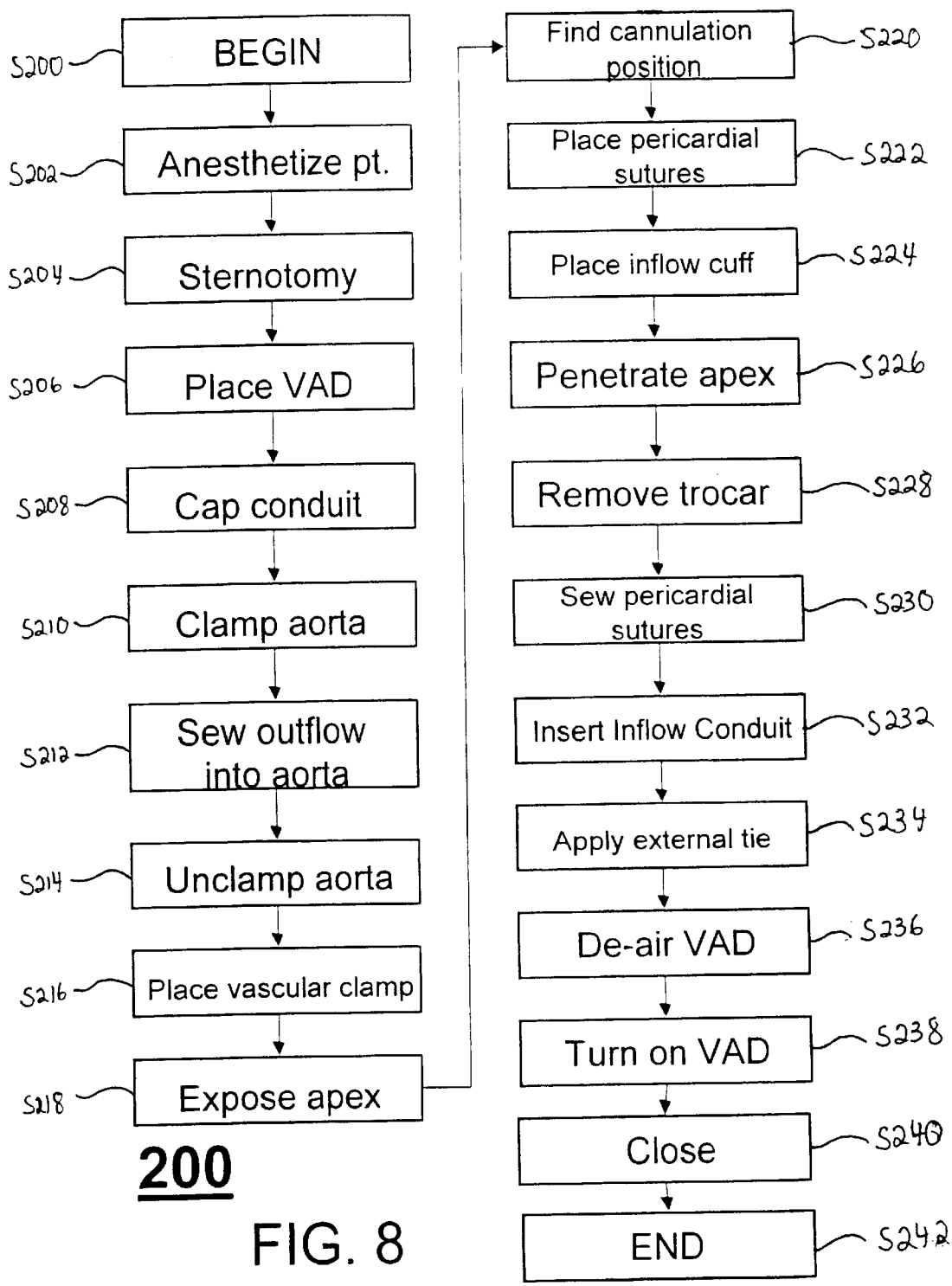
FIG. 8 is a flow diagram illustrating a method for apical cannulation of the heart without cardiopulmonary bypass.

Method 200 of FIG. 8 begins at S200, the patient is anesthetized at S202 and a median sternotomy is performed at S204. A NOVACOR® left ventricular assist system (Baxter Healthcare Corporation) is placed in the abdominal wall at S206, and the inflow conduit 18 is capped off at S208 to prevent fat or other surgical debris from contaminating it. A "side biting" clamp is applied to the aorta at S210, and the outflow conduit 26 from the NOVACOR® device is sewn into the aorta at S212. Once the "side biting" clamp is removed at S214, a vascular clamp is placed across the distal portion of the outflow conduit at S216, thus allowing the outflow conduit to de-air. Following the proper insertion of the outflow conduit 24, the apex 14 of the heart is exposed at S218.

Once the apex 14 is exposed, the position at which the apex 14 is to be cannulated is determined at S220. After the cannulation position is determined at S220, pericardial sutures 22 are placed around the determined cannulation position at S222. Note that at this stage, no hole is made in the apex. Typically, it takes several minutes to locate the cannulation position in the apex 14 and to place the required pericardial sutures 22, however, because the heart is still beating and the patient has circulation, this action is not time-critical.

Referring once again to method 200 of FIG. 8, at S224, the surgeon places the center of the inflow cuff/trocar assembly 50 over the identified cannulation position so that it is centered with the pericardial sutures 22 spaced evenly around it. At S226, the surgeon quickly penetrates the apex 14 with the trocar 38 and seats the inflow cuff 16 so that its sewing ring 20 abuts the apex 14.

Figure 9:
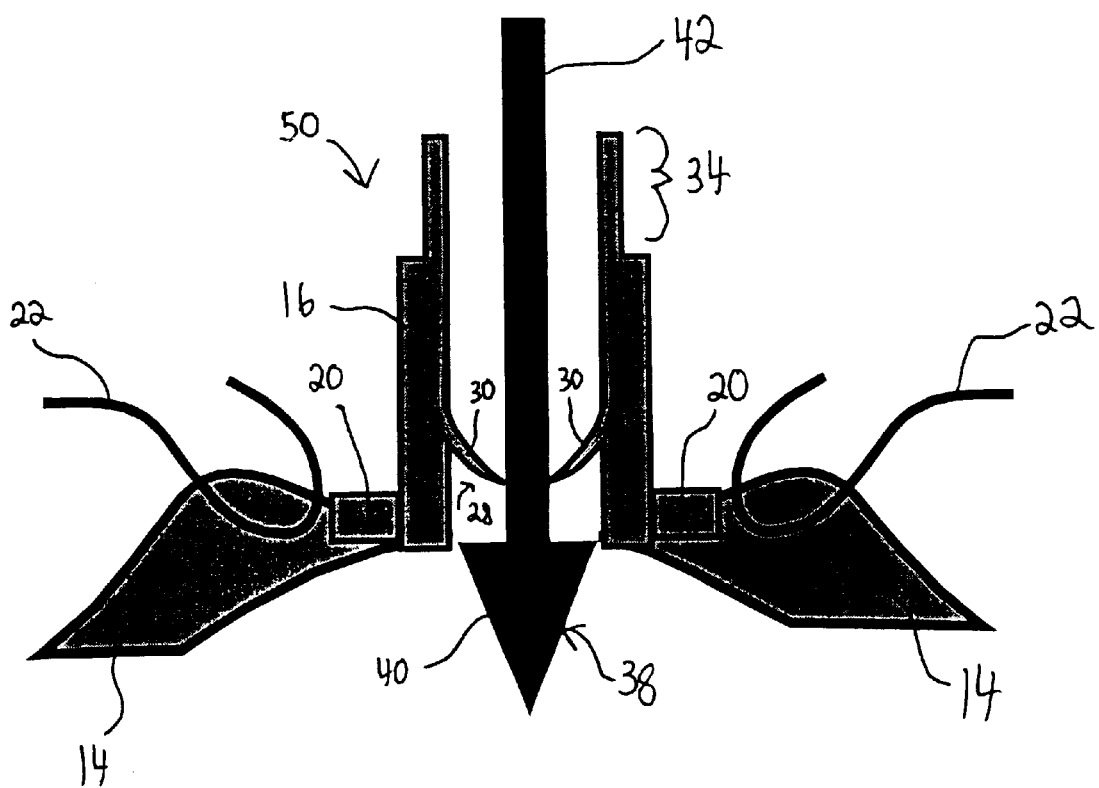
FIG. 9 is a sectional view of an inflow cuff and trocar according to the present invention, illustrating the penetration of the apex.

The penetration of the trocar 38 (i.e., at S226) is illustrated in the sectional view of FIG. 9. In FIG. 9, the pericardial sutures 22 have not yet been sewn to the sewing ring 20, and protrude loosely from the apex 14. The diameter of the hole in the apex 14 is approximately 2 cm, and the diameter of the inflow cuff 16 is approximately 1.9 cm. These measurements may vary, as both devices may be manufactured in a variety of sizes to accommodate different size patients.

Trocar 138 would penetrate into the apex 14 essentially the same distance as trocar 38 of FIG. 9. As in FIG. 9, the leaves 130 of the unidirectional valve 128 would make a seal around the handle portion 142 of the trocar 138. However, when a certain trocar 138 depth was reached, the flange 143 on the handle portion 142 would abut the narrowed portion 130 of the inflow cuff 116, preventing the trocar 138 from being inserted any further into the apex 14. If the flange 143 is attached to the handle portion 142 by set screws or other fasteners, the physician would adjust the maximum penetration depth of the trocar 138 by adjusting the position of the flange 143 prior to the surgical procedure.

Referring again to method 200 of FIG. 8, the trocar 38 is removed at S228 of method 200 by pulling on its handle portion 42. Following the removal of the trocar 38, at S230, the pericardial sutures 22 are sewn into the sewing ring 20 of the inflow cuff 16 so that the inflow cuff 16 is retained in place.

At S232 of method 200, the inflow conduit 18 from the NOVACOR® device is inserted into the inflow cuff 16. In the time interval between the penetration of the trocar 38 and the insertion of the inflow conduit 18 (i.e., the time interval between the execution of S226 and S232), the unidirectional valve 28 of the inflow cuff 16 prevents the patient from exsanguinating. A surgeon would be able to perform the actions of S226–S232 in approximately three minutes.

It should be understood that the leaves 30 of the unidirectional valve 28 are not required to make a completely blood-tight seal during this period (S226–S232), because some slight leakage of blood may help to de-air the inflow cuff 16. However, the seal made by the leaves 30 should be sufficient to prevent most of the blood from leaking. At S234, an external tie 23 is applied to the inflow cuff 16 to retain the inflow conduit 18, and is tightened appropriately.

If the seal made by the leaves 30 was required to be completely blood-tight to accommodate a particular procedure, the leaves 30 could be reinforced with a woven mesh of synthetic threads, in much the same way as the body of the inflow cuff 16, or a material with a greater stiffness could be chosen for the leaves 30. Leaves 30 having greater stiffness would deflect less in response to the pressure exerted by the blood in the heart 10, and would thus form a tighter seal. In general, the leaves 30 should have sufficient stiffness (i.e., the material should have a sufficiently high elastic modulus) such that they do not deflect enough to open the unidirectional valve 28 when exposed to an operating pressure equal to a patient's systolic blood pressure. However, the leaves 30 should be compliant enough to permit the trocar 38 to be drawn through the unidirectional valve 28 quickly and smoothly at S228. If S228 is significantly delayed (e.g., the trocar 38 snags on one of the leaves), blood could escape from the unidirectional valve 28.

Referring again to method 200 of FIG. 8, the surgeon allows blood to egress the NOVACOR® device through the outflow conduit 24 to completely de-air the NOVACOR® device at S236. The NOVACOR® device is turned on at S238, and the surgeon performs the normal closing procedures at S240. Method 200 completes at S242.

Figure 10:
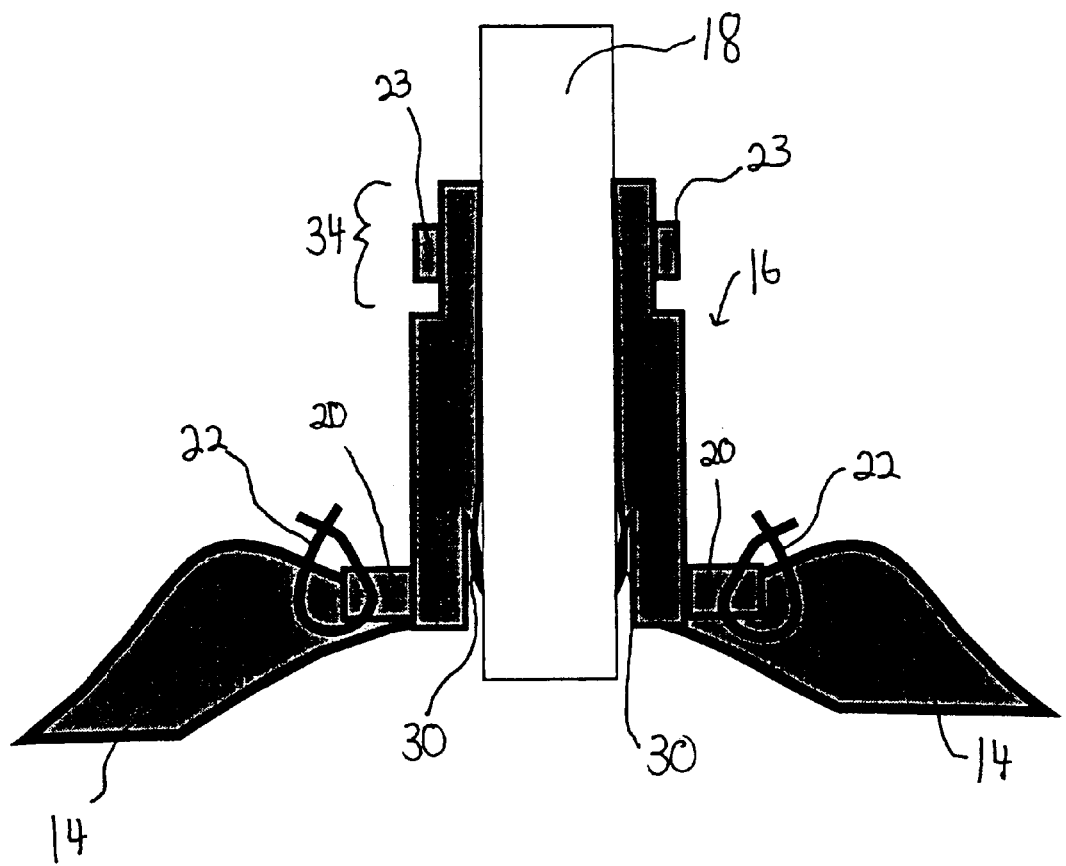
FIG. 10 is a sectional view of the inflow cuff with inserted inflow conduit, through line 2—2 of FIG. 1.

After the inflow conduit 18 is inserted into the inflow cuff 16, all blood passes through the lumen of the inflow conduit 18, and thus, the unidirectional valve 28 is no longer exposed to pressure. FIG. 10 is a sectional view of the completed inflow cuff/inflow conduit assembly through line 2—2 of FIG. 1. As shown, the narrowed portion 34 of the inflow cuff 16 is cinched around the protruding inflow conduit 18 by the tie 23. The leaves 30 of the unidirectional valve 28 have been displaced by the insertion of the inflow conduit 18 and are compressed against the internal walls 32 of the inflow cuff 18.

FIG. 10 contemplates that the leaves 30 will be neatly compressed against the internal walls 32 of the inflow cuff 16, although the actual position and final bias of the leaves 30 is immaterial, so long as they do not compress the inflow conduit 18, or otherwise occlude the blood flow through the inflow conduit 18. However, with the inflow cuff 116, the increased thickness of the leaves 130 makes their final disposition more of an issue, since there may not be enough space in the lumen of the inflow cuff 116 for the leaves 130 to deflect completely out of the path of the inflow conduit 18.

Figure 11:
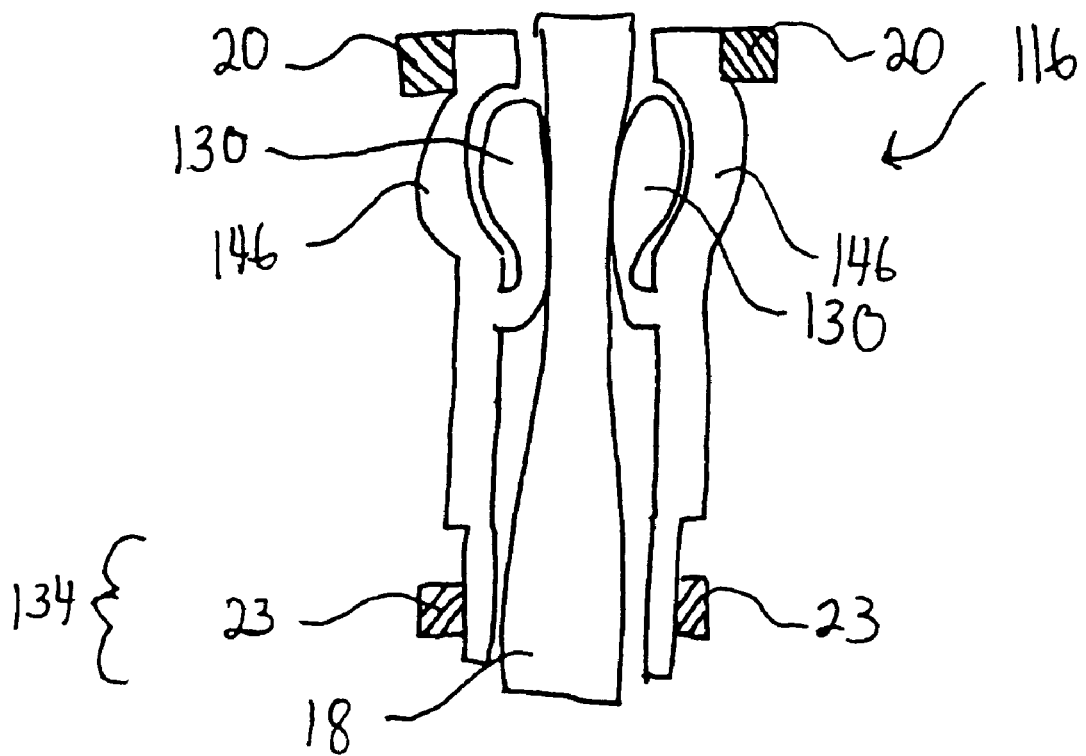
FIG. 11 is a sectional view of an inflow cuff with inserted inflow conduit according to the third embodiment of the present invention, through line 2—2 of FIG. 1.

To provide more space for the "storage" of the leaves 130 once the inflow conduit 18 is inserted, the inflow cuff 116 could be provided with a bulge 146 in its crosssection, between the sewing ring 20 and the location of the valve 128. This concept is illustrated in FIG. 11, a sectional view of the inflow cuff 116 with the inflow conduit 18 installed. Those skilled in the art will realize that the bulge 146 must be carefully designed, as the inclusion of a bulge increases the chances that the inflow cuff 116 may experience a "column buckling" effect, which would cause its lumen to collapse, potentially occluding flow through the inflow conduit 18. Preferably, the bulge 146 would be reinforced with several layers of woven mesh.

Because blood passes through the inflow conduit 18 once it is inserted into the inflow cuff 16, 116, the valve 28, 128 does not present issues of blood stagnation or backflow, as are common with synthetic valves used in medical devices. Depending on the particular model of VAD that is employed, the patient may need to be placed on long-term anticoagulant therapy, but the use of an inflow cuff 16, 116 per se would not create a need for such therapy.

Preferably, the inflow cuff 16, 116 and associated trocar 38, 138 are produced in a variety of sizes and dimensions in order to accommodate various patient sizes and the different dimensions required for the various VAD models. If the materials for the inflow cuff 16, 116 are chosen appropriately (e.g., silicone main body with woven, reinforced sections), then the inflow cuff 16, 116 may be manufactured by molding it as a single piece.

While the invention has been described in detail and with reference to specific embodiments thereof, it will be apparent to those of ordinary skill in the art that various changes and modifications can be made without departing from the spirit and scope thereof.

What is claimed is:

1. An inflow cuff assembly for beating-heart apical cannulation of a heart, comprising:
    a tube having a first end and a second end and a lumen defined therethrough, said first end constructed and adapted to be inserted into the heart;
    a valve disposed on and integral with the interior of said tube, said valve having two or more compliant leaves constructed and adapted to form a releasable seal with one another, said valve (1) preventing blood flow out of the heart when closed and (2) opening in response to pressure directed towards the heart;
    trocar for selective insertion through-its the lumen of said tube, the trocar constructed and arranged to form a hole in the heart of sufficient size to admit the first end of said tube; and
    synthetic conduit constructed and arranged for selective insertion into the lumen of said tube to open said valve and to establish a route for blood flow out of the heart.

2. The inflow cuff assembly of claim 1, comprising a sewing ring disposed on an exterior surface of said tube proximate to said first end, said sewing ring constructed and adapted to be sutured to an exterior wall of the heart and to retain the first end of said tube at a selected position in the heart, said valve being disposed further from the first end of said tube than said sewing ring.

3. The inflow cuff assembly of claim 2, wherein the valve has three compliant leaves, and wherein said tube includes a preformed bulged portion in the walls thereof, a bulged portion disposed at a location between said sewing ring and said valve such that said three compliant leaves fit into said bulged portion upon the insertion of the conduit.

4. The inflow cuff assembly of claim 2, wherein the sewing ring is comprised of synthetic, biocompatible felt.

5. The inflow cuff assembly of claim 1, wherein the tube is formed from synthetic material.

6. The inflow cuff assembly of claim 5, wherein the tube is manufactured of a biocompatible, silicone rubber, wherein the silicone rubber is selectively reinforced by a woven mesh.

7. A medical device which may be inserted into the heart of a patient to provide a passageway for blood flow, comprising:
    an inflow cuff having a lumen and a valve, wherein said valve (1) prevents blood from flowing out of the heart when closed and (2) opens in response to pressure in the lumen directed inward toward the heart;
    a trocar which is inserted longitudinally through the lumen of said inflow cuff and protrudes beyond an insertion end of said inflow cuff, said trocar being retractable and removable from the lumen of said inflow cuff; and
    a synthetic conduit constructed and arranged for selective insertion into the lumen of said tube to open said valve and to establish a route for blood flow out of the heart.

8. The medical device of claim 7, wherein said valve is comprised of at least two leaves, each of said at least two leaves integrally formed with an interior wall of said inflow cuff and having free ends, said free ends abutting and forming a releasable seal with one another.

9. The medical device of claim 8, further comprising a sewing ring disposed on an outer surface of said inflow cuff, said sewing ring allowing said inflow cuff to be secured to an exterior portion of the heart.

10. The medical device of claim 9, wherein said sewing ring comprises a synthetic, biocompatible felt composed of woven tetrafluoroethylene strands.

11. The medical device of claim 10, wherein said sewing ring comprises a synthetic, biocompatible felt composed of woven polyester strands.

12. The medical device of claim 11, wherein the conduit is the inflow conduit of a ventricular assist device.

13. The medical device of claim 12, wherein said inflow cuff is molded from a biocompatible, silicone rubber.

14. The medical device of claim 13, wherein the biocompatible, silicone rubber is reinforced with a woven mesh of synthetic strands.

15. The medical device of claim 14, wherein said inflow cuff and the conduit are sized such that there is substantially no clearance between the interior of said inflow cuff and the conduit when the conduit is inserted therein.

16. The medical device of claim 15, wherein the conduit is retained in said inflow cuff by an external tie secured around an exterior portion of said inflow cuff.

17. The medical device of claim 16, wherein said sewing ring is located closer to the insertion end of said inflow cuff than said valve.

18. The medical device of claim 7, wherein the trocar further comprises a flange, said flange preventing the longitudinal insertion of the trocar beyond a selected point.

19. A method of providing a passageway for blood flow out of a heart, comprising:
    inserting an inflow cuff into the apex of heart, the inflow cuff including a tube having a first end and a second end and a lumen defined therethrough, said first end constructed and adapted to be inserted into the heart; a sewing ring disposed on an exterior surface of said tube proximate to said first end, said sewing ring constructed and adapted to be sutured to an exterior wall of the heart and to retain the first end of said tube at a selected position in the heart; and a valve disposed on and integral with the interior of said tube, said valve having two or more compliant leaves constructed and adapted to form a releasable seal with one another, said valve (1) preventing blood flow out of the heart when closed and (2) opening in response to pressure directed towards the heart;
    said inserting including inserting a trocar through the lumen of said tube, the trocar constructed and arranged to form a hole in the heart of sufficient size to admit the first end of said tube;
    retracting said trocar and removing it from said tube; and
    inserting a synthetic conduit through the lumen of said tube to open said valve and to establish a route for blood flow out of the heart.

20. The method of claim 19, further comprising:
    securing said sewing ring to the heart; and
    applying an external tie to an exterior surface of said inflow cuff to retain the conduit within said inflow cuff.

* * * * *